United States Patent
Shimobayashi

(10) Patent No.: US 9,986,894 B2
(45) Date of Patent: Jun. 5, 2018

(54) CONNECTOR

(71) Applicant: OLYMPUS CORPORATION, Tokyo (JP)

(72) Inventor: Koji Shimobayashi, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 0 days. days.

(21) Appl. No.: 15/647,379

(22) Filed: Jul. 12, 2017

(65) Prior Publication Data

US 2017/0303772 A1    Oct. 26, 2017

Related U.S. Application Data

(63) Continuation of application No. PCT/JP2016/060195, filed on Mar. 29, 2016.

(30) Foreign Application Priority Data

Apr. 30, 2015   (JP) .................................. 2015-093182

(51) Int. Cl.
   *A61B 1/00*   (2006.01)
   *G02B 6/38*   (2006.01)

(52) U.S. Cl.
   CPC ...... *A61B 1/00121* (2013.01); *A61B 1/00066* (2013.01); *G02B 6/3831* (2013.01)

(58) Field of Classification Search
   CPC ........... A61B 1/00121–1/00126; G02B 6/3831
   See application file for complete search history.

(56) References Cited

U.S. PATENT DOCUMENTS

| 2002/0098732 | A1  | 7/2002 | Shimizu |
| 2004/0157499 | A1* | 8/2004 | Nania ................ H01R 13/6271 439/680 |
| 2011/0071349 | A1* | 3/2011 | Drontle .............. A61B 1/00165 600/106 |

FOREIGN PATENT DOCUMENTS

| JP | S58-27870    | 2/1983 |
| JP | 2001-104250 A | 4/2001 |
| JP | 2001-258831 A | 9/2001 |

(Continued)

OTHER PUBLICATIONS

International Search Report dated Jun. 14, 2016 issued in PCT/JP2016/060195.

(Continued)

*Primary Examiner* — Omar R Rojas
(74) *Attorney, Agent, or Firm* — Scully, Scott, Murphy & Presser, P.C.

(57) ABSTRACT

A connector comprises an upper surface finger-resting portion that extends in the longitudinal axial direction on the outer periphery of the gripping portion, and on which the first finger is placed, a lower surface finger-resting portion on which the second finger or the third finger is rested when the connector is gripped by placing the first finger on the upper surface finger-resting portion, and a guide protrusion portion that is arranged on the same straight line as the upper surface finger-resting portion in the longitudinal axial direction and determines the position to be inserted, in which the connector is directly fitted into the receiving-side connector by directing the finger tip of the first finger that is placed on the upper surface finger-resting portion to the guide groove of the receiving-side connector and inserting the connector.

4 Claims, 5 Drawing Sheets

(56) References Cited

FOREIGN PATENT DOCUMENTS

| JP | 2002-216902 A | 8/2002 |
| JP | 2008-055130 A | 3/2008 |
| JP | 2013-208187 A | 10/2013 |
| WO | WO 2007/043257 A1 | 4/2007 |

OTHER PUBLICATIONS

Japanese Office Action dated Nov. 29, 2016 issued in JP 2016-553908.
English translation of International Preliminary Report on Patentability dated Nov. 9, 2017 together with the Written Opinion received in related International Application No. PCT/JP2016/080195.

\* cited by examiner

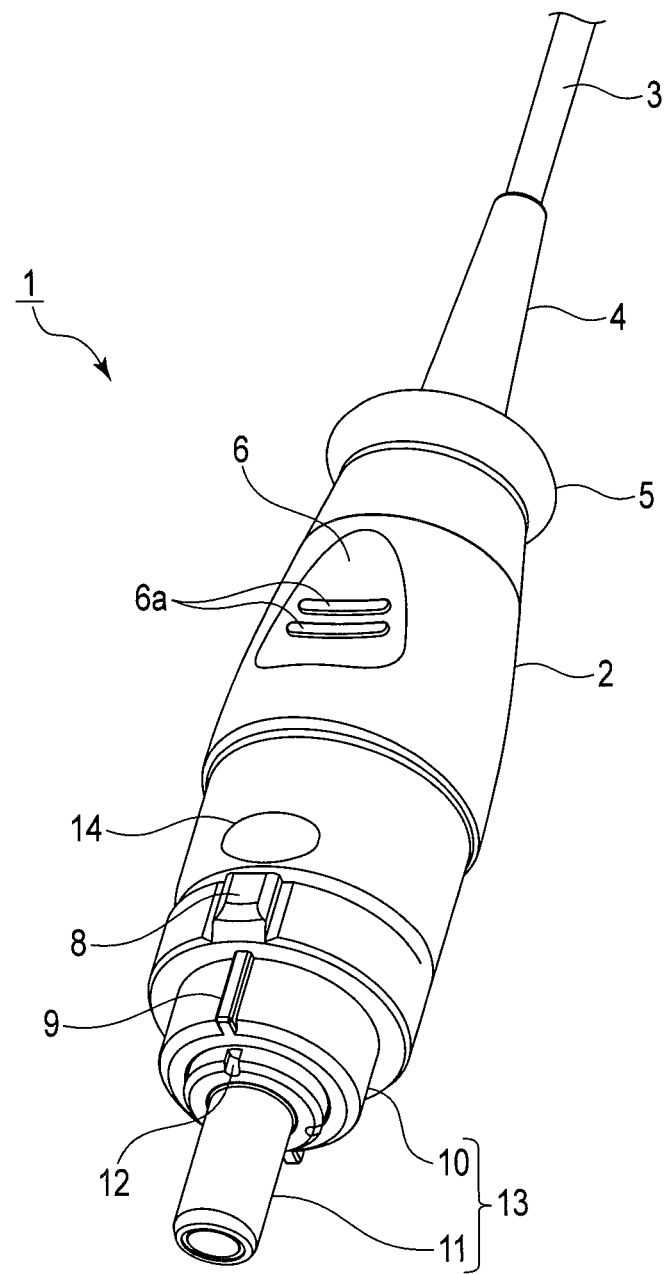
F I G. 1

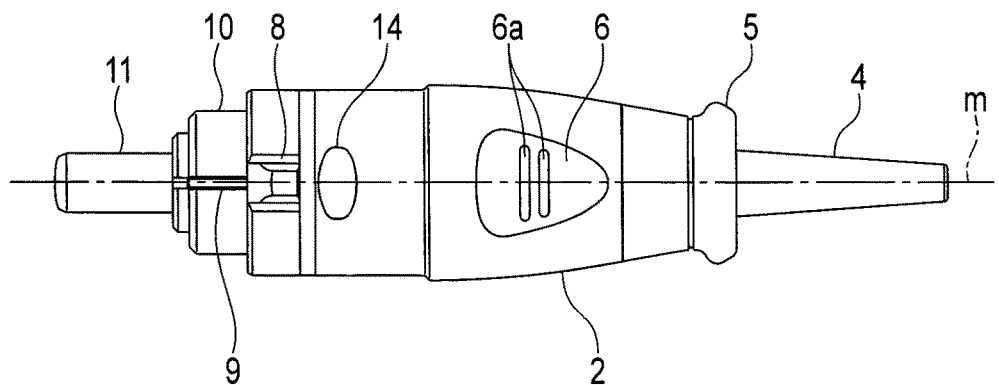
F I G. 2A
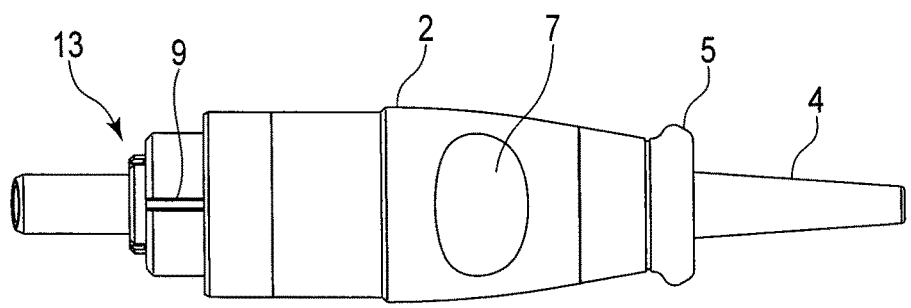
F I G. 2B
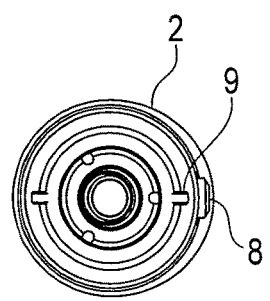
F I G. 2C

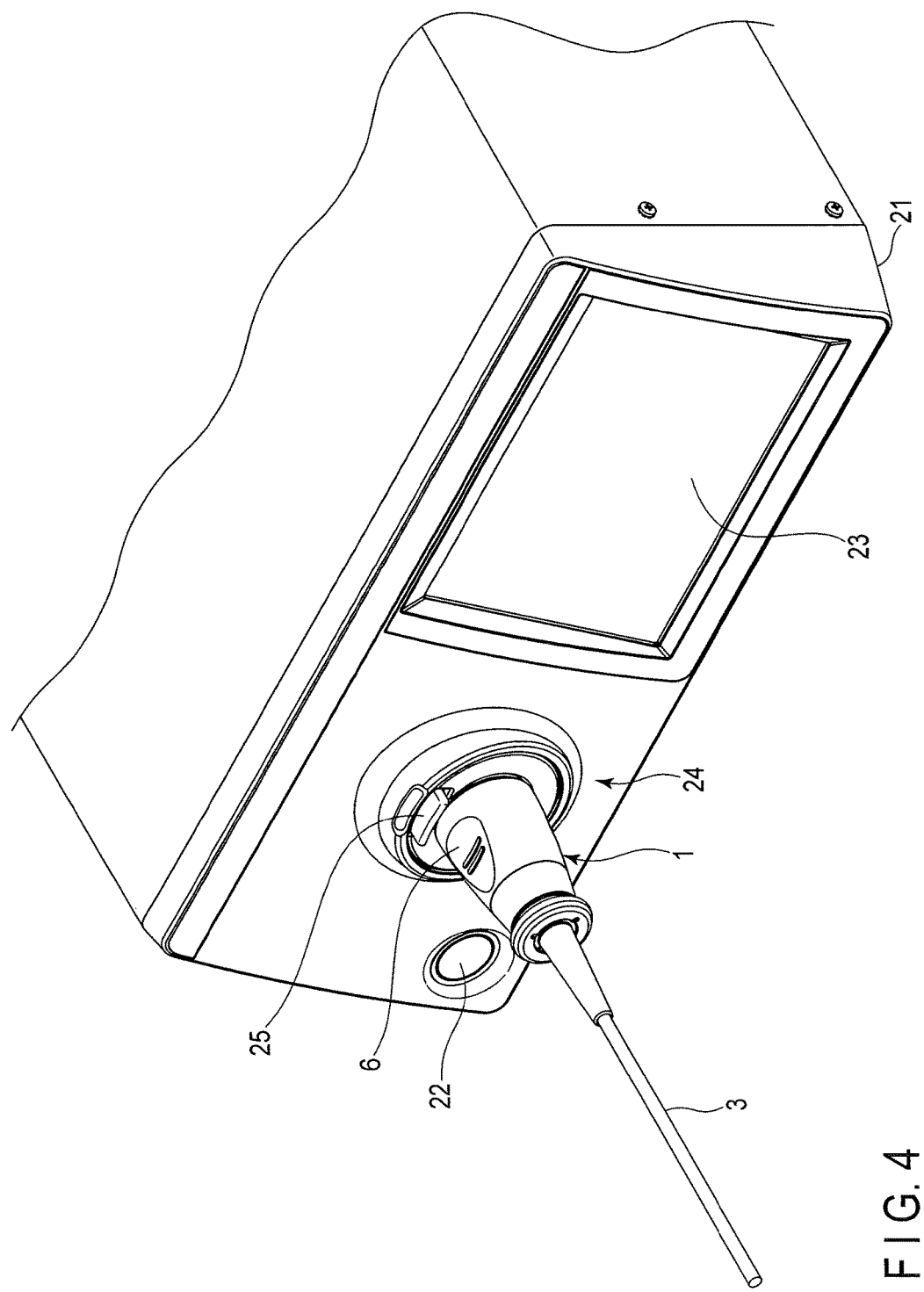
F I G. 4

CONNECTOR

CROSS-REFERENCE TO RELATED APPLICATIONS

This is a Continuation Application of PCT Application No. PCT/JP2016/060195, filed Mar. 29, 2016, which was published under PCT Article 21 (2) in Japanese. This application is based upon and claims the benefit of priority from prior the Japanese Patent Application No. 2015-093182, filed Apr. 30, 2015 the entire contents of which are incorporated herein by references.

BACKGROUND OF THE INVENTION

1. Field of the Invention

The present invention relates to a connector provided at a cable end to be connected to an apparatus.

2. Description of the Related Art

Generally, a detachable connector is provided on a cable to be connected to the apparatus. In this cable, an electric wiring, an optical fiber, or a tube, etc. for transmitting or conveying electricity, light, and fluent materials (for example, liquid and gas, etc.) are installed. In order to simplify a connecting operation and reduce the number of cables, a composite cable, in which a wiring and a tube, etc. are combined and installed within one cable, is frequently used.

Normally, a fitting guide is provided on a connector that is provided on an electric wiring cable so that the terminals (or electrodes) are electrically connected only by inserting the guide into a receiving-side connector attached to the apparatus. This allows the connector to be guided to a correct connecting position upon insertion. In the case of a connector with a rectangular connecting surface that is connected to a video processor as disclosed in Jpn. Pat. Appln. KOKAI Publication No. 2008-5130 (Patent Literature 1), by forming each fitting portion of a concave part and a convex part provided on the connecting surface in a trapezoidal geometry, a configuration that allows fitting only at a limited position will be obtained.

BRIEF SUMMARY OF THE INVENTION

According to an embodiment of the present invention, there is provided a connector comprising: a gripping portion of a cylindrically-shaped connector; an upper surface finger-resting portion that is formed of a concave surface extending in a longitudinal axial direction on an outer periphery of the gripping portion, and on which a first finger is placed when being gripped; a lower surface finger-resting portion that is formed of a concave surface extending in a direction intersecting the longitudinal axial direction on the opposite side of the upper surface finger-resting portion with respect to the longitudinal central axis, and on which one of a second finger and a third finger is rested when the connector is gripped in a state where the first finger is placed on the upper surface finger-resting portion; an insertion portion that is arranged on a distal end side of the gripping portion, and is inserted into a receiving-side connector into which the insertion portion is to be fitted; and a guide protrusion portion which is arranged on a same straight line as the upper surface finger-resting portion in the longitudinal axial direction, and which determines a position of the inserted insertion portion.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 1 is a diagram showing an exterior configuration of a connector according to an embodiment.

FIG. 2A is an external view of the connector when observed from the front.

FIG. 2B is an external view of the connector when observed from underneath.

FIG. 2C is an external view of the connector when observed from a connecting terminal side.

FIG. 4 is an external view showing a state in which the connector is fitted to a camera control unit.

DETAILED DESCRIPTION OF PREFERRED EMBODIMENTS

An embodiment of the present invention will be explained in detail with reference to the accompanying drawings.

Figure 2D:
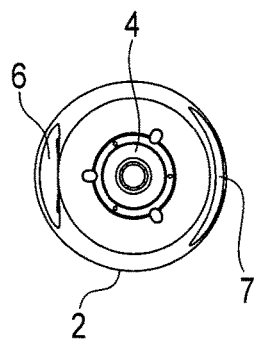
FIG. 2D is an external view of the connector when observed from a cable side.
Figure 3:
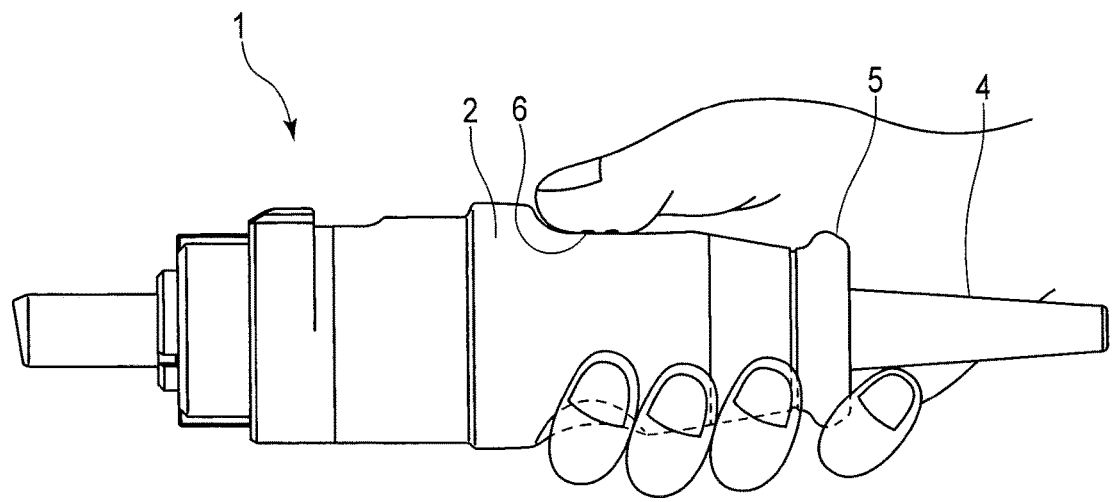
FIG. 3 shows a state of the connector when being held.

FIG. 1 is a diagram showing an exterior configuration of a connector according to an embodiment. FIG. 2A is an external view of the connector when observed from the front, FIG. 2B is an external view of the connector when observed from underneath, FIG. 2C is an external view of the connector when observed from a connecting terminal side, and FIG. 2D is an external view of the connector when observed from a cable side. FIG. 3 shows a state of the connector when being held. In the following explanation, the side of the connector to be fitted to another connector will be referred to as the distal-end side or the front, and the side of the connector from which a cable is extended will be referred to as the rear-end side or the rear. Furthermore, a direction in which the cable is extended in the connector will be referred to as a longitudinal direction or a longitudinal axial direction. The upper surface and the lower surface of the connector according to the present embodiment are such that, in the case where a given portion in a radial direction of the connector is defined as the upper surface, the opposite side with respect to the longitudinal axis center is regarded as the lower surface. In the present embodiment, a position where an upper surface finger-resting portion 6 mentioned later on is provided, is explained as the upper surface.

A connector 1 of the present embodiment will be explained as an example of a connector provided at a camera cable end that includes a fiber cable that guides light of an optical signal including image information, and an electric wiring cord that transmits/receives an electric signal. The present invention is technically characterized in its structure regarding the profile of the connector. Therefore, what is to be transmitted or conveyed is one of electricity, light, and a fluent material, or the combination thereof; however, is not particularly limited.

An insertion portion 13 is provided on the fitting side of the connector 1. The insertion portion 13 comprises a light connecting portion 11 that is arranged in the center and conveys light, such as laser light, and a circular cylindrical shape electrode portion 10 annularly arranged around the light connecting portion 11, and on the outer periphery of which a plurality of electrodes are formed.

At least one guide protrusion portion 9 is formed in a longitudinal axial direction on the outer periphery of the electrode portion 10. On a receiving-side connector that is not shown, a guide groove (not shown) that fits with this guide protrusion portion 9A is formed to be paired with the guide protrusion portion 9. The guide protrusion portion 9 and the guide groove are inserted by sliding in a fitted state; and, upon connector connection, serve as a guide to bring predetermined electrodes into contact with each other for electrical connection.

Furthermore, a plurality of aligning grooves 12 are provided around the proximal end side of the light connecting portion 11 so that an appropriate optical connection is achieved upon connector connection. By forming protrusions (not shown) to be paired with the aligning grooves 12 on the receiving-side connector, appropriate aligning may be completed when the connector is inserted, and each of the protrusions and the aligning grooves 12 are fitted. Here, an example of providing three aligning grooves 12 in regular intervals is shown. It is favorable to have a plurality of pieces of the aligning grooves 12 formed at intervals.

The diameter rearward of this insertion portion 13 increases in steps, and is connected to a gripping portion 2 which is a connector main body. A grip end 5 that has a semicircle cross-sectional surface and is protruded brim-like is provided on the circumferential surface at the rear end of the gripping portion 2. In a state where the gripping portion 2 is gripped by hand, as shown in FIG. 3, the grip end 5 is positioned on the palm and, for example, placed between the fourth finger (digitus annularis) and the fifth finger (digitus minimus). A bending stopper 4 is provided on the rear-end side of the grip end 5, and a cable 3 extends from the inside of the bending stopper 4 to the rear-end side. As mentioned above, the cable 3 is a cable for cameras, which include, for example, an optical fiber and an electric wiring cord. Furthermore, a locking portion 8 protruding in a rectangular shape is provided on the outer periphery of the distal-end side of the gripping portion 2. An upper surface indicator 14 which is formed of a visibly recognizable mark (or a symbol or color notation) and indicates the position of the upper surface of the connector is arranged adjacent to the locking portion 8 and rearward in the longitudinal axial direction.

As shown in FIG. 3, in a state where the gripping portion 2 is gripped by hand, the upper surface finger-resting portion 6 on which a first finger (thumb) extended in the longitudinal axial direction be placed or be rested is provided at approximately the center of the gripping portion 2. As shown in FIG. 2A, this upper surface finger-resting portion 6 is formed as a concave surface which is curved in the shape of the pad of the thumb. As shown in FIG. 2A, upper surface recognition portions 6a, which can be recognized by feel on the pad of the rested finger, are formed on the surface within the concave surface. In the illustrated example, two parallel linear protruded portions (convex shape portions) are formed. The shape of this upper surface recognition portions 6a are, of course, not limited to the illustrated linear shape, and may also be in various shapes such as in a waveform shape, a cylindrical shape, or a dome shape, as long as they are in shapes where the presence can be recognizable by feel on the finger pad. The upper surface recognition portions 6a do not necessarily have to protrude; the upper surface recognition portions 6a may be grooved or shaped as concaved holes (concave shape portions), or may be both a convex shaped portion and a concave shaped portion.

Figure 5:
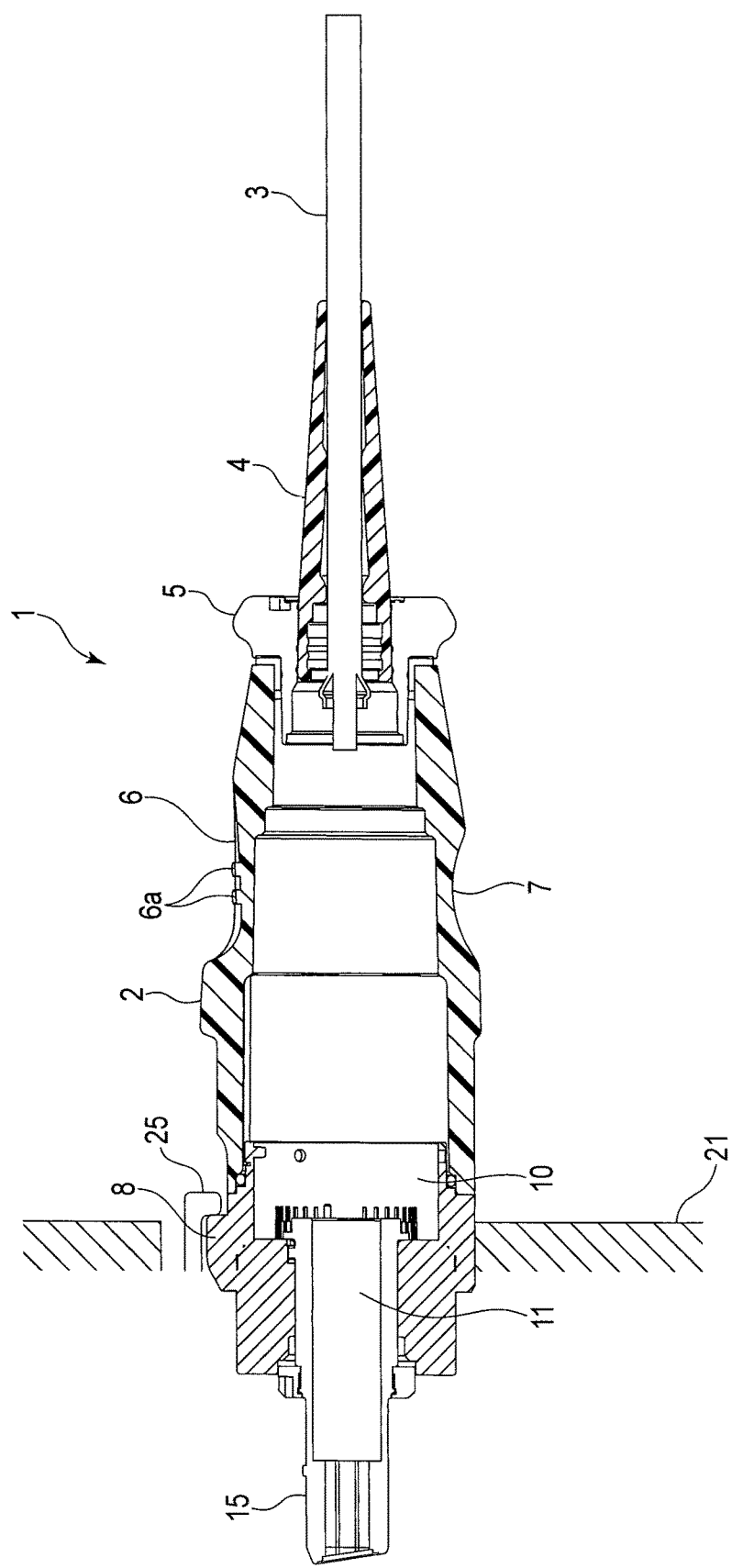
FIG. 5 is a longitudinal sectional view of the connector in a fitted state.

FIG. 4 shows a part of a camera control unit (CCU) of an endoscope device as an example of the apparatus to which the connector 1 is connected. FIG. 5 is a cross-sectional view showing a configuration of a longitudinal sectional view of the connector 1 in a state where it is fitted into the receiving-side connector.

On the front surface of the camera control unit 21, an electric power switch 22, a connector receiving portion 24, and an operation touch panel 23 are provided. Menus and selection items necessary for operation are displayed on the operation touch panel 23, and photographing conditions, etc. are set by an instruction operation. A receiving-side connector 15 is provided on the connector receiving portion 24. In order to have the connector 1 maintained in a fitted state, a locking hook portion 25 that retains the locking portion 8 and prevents the connector 1 from falling off is provided on the receiving-side connector 15.

This locking hook portion 25 is configured movable in a radial direction of the receiving-side connector 15, and is biased in a direction towards the central direction. When the connector 1 is inserted and moved, the locking hook portion 25 is pushed up by the distal end side of the locking portion 8 and slides on the upper surface. When the fitting is completed, the locking hook portion 25 retains the corner on the rear-end side of the locking portion 8 and fixes the connector 1 so as not to fall off from the receiving-side connector 15. The locking portion 8 and the upper surface finger-resting portion 6 are arranged apart by a distance where the finger tip does not come in contact with the locking hook portion 25 when the finger is placed on the upper surface finger-resting portion 6 to insert the connector 1, and the locking hook portion 25 performs a lock operation. Therefore, if the connector 1 is inserted by placing the finger on the upper surface finger-resting portion 6, an unfortunate situation such as the finger tip being caught in the locking hook portion 25 can be prevented.

A lower surface finger-resting portion 7 is formed on the opposite side of the upper surface finger-resting portion 6 with reference to the longitudinal central axis, and at a position where at least a tarsus and a middle articulation of the second finger (index finger) or the third finger (middle finger) are rested in a state where the first finger (thumb) is placed on the upper surface finger-resting portion 6 and grips the gripping portion 2 shown in FIG. 3. As shown in FIG. 2B, the lower surface finger-resting portion 7 extends in a circumferential direction intersecting the longitudinal axial direction; that is, formed to be a horizontally long groove-like concave surface along the outer periphery of the gripping portion 2. In the present embodiment, the lower surface finger-resting portion 7 is formed by one groove, but may also be configured by a plurality of grooves separated for each finger.

As shown in FIG. 3, in a state where the connector is gripped by placing the first finger on the upper surface finger-resting portion 6, the first finger is directed in the longitudinal axial direction. However, the second finger or the third finger is wound around the gripping portion 2 in a circumferential direction, and is directed in a direction intersecting the longitudinal axial direction (for example, a direction approximately orthogonal to the longitudinal axial direction). Therefore, in the present embodiment, in accordance with the direction of these fingers, the upper surface finger-resting portion 6 is formed in a curved concave shape (a longitudinal concave shape) extending in the longitudinal axial direction, and the lower surface finger-resting portion 7 is formed in a curved grooved shape (a horizontally long groove shape) extending in a circumferential direction intersecting the longitudinal axial direction.

The upper surface finger-resting portion 6, the upper surface index 14, the locking portion 8, and the guide protrusion portion 9 (one of the guide protrusion portions 9 of the two guide protrusion portions 9 shown in FIG. 2A) are arranged in a manner that each center thereof is aligned on a straight line m along the longitudinal axial direction on the upper surface of the gripping portion 2 shown in FIG. 2A. In other words, the guide protrusion portion 9 is arranged on the same straight line as the upper surface finger-resting portion 6 in the longitudinal axial direction.

When attaching the receiving-side connector 15 on a chassis of the camera control unit 21, by aligning the guide groove to be fitted into the guide protrusion portion 9 at a predetermined position set in advance, such as at a position of the locking hook portion 25, an operator will be able to ascertain an approximate position of the guide groove. Furthermore, separately, a mark indicating the position of the guide groove may also be annotated in the vicinity of the connector receiving portion 24.

In the present embodiment, since it is already known that the guide groove is arranged on the same longitudinal axis as the locking hook portion 25, the position of the guide groove can be assumed from the locking hook portion 25. Accordingly, since the position of the guide protrusion portion 9 is on the extension of the upper surface finger-resting portion 6, when the operator grips the connector by placing the first finger on the upper surface finger-resting portion 6 and resting the second finger or the third finger on the lower surface finger-resting portion 7, the positions of the guide protrusion portion 9 and the guide groove can be matched and fitted by inserting the insertion portion 13 into the receiving-side connector 15 by directing the distal end (finger tip) of the first finger to the locking hook portion 25. Therefore, the connector can be inserted directly without being turned to find a matching position.

In the above manner, the operator is able to sensitively ascertain the position of the guide protrusion portion 9 only by gripping the connector in an easily held manner (that is, holding the connector by placing the first finger on the upper surface finger-resting portion 6, and resting the second finger and the third finger on the lower surface finger-resting portion 7). Furthermore, only by inserting the connector by directing the finger tip of the first finger to a preset position of the guide groove of the receiving-side connector (for example, an upper side) or a mark, the connector can be easily fitted and connected without being rotated to find a fitting position.

The present invention provides a connector that has a finger resting portion matching the shape of a finger holding the connector, and, in a state of being held, allows positional relationship with a fitting destination to be ascertained.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

The invention claimed is:
1. A connector comprising:
a gripping portion that has, on a distal end side thereof, an insertion portion to be inserted into a receiving-side connector;
an upper surface finger-resting portion that is formed of a first concave surface extending in a longitudinal axial direction on an outer periphery of the gripping portion, and on which a first finger is placed when being gripped;
a lower surface finger-resting portion that is formed of a second concave surface extending in a direction intersecting the longitudinal axial direction on an opposite side of the upper surface finger-resting portion with respect to a longitudinal central axis, and on which one of a second finger and a third finger is rested when the connector is gripped in a state where the first finger is placed on the upper surface finger-resting portion;
a guide protrusion which is arranged on a same straight line as the upper surface finger-resting portion in the longitudinal axial direction, and which determines a position of the inserted insertion portion; and
a locking portion that is arranged between the upper surface finger-resting portion and the guide protrusion on a same straight line in the longitudinal axial direction, the locking portion engaging with a locking hook portion provided on the receiving-side connector when fitted into the receiving-side connector, thereby fixing the insertion portion.

2. The connector according to claim 1, wherein the insertion portion is fitted into the receiving-side connector by directly fitting the guide protrusion into a guide groove by directing a finger tip of the first finger that is placed on the upper surface finger resting portion to the guide groove that is formed on the receiving-side connector, is capable of being fitted into the guide protrusion, and is arranged at a given position.

3. The connector according to claim 1, comprising an upper surface recognition portion that is formed on the surface of the upper surface finger-resting portion, and has at least one of a concave-shaped portion or a convex-shaped portion whose presence, when the first finger is placed thereon, is recognizable by a finger pad.

4. The connector according to claim 1, wherein the locking portion and the upper surface finger-resting portion are arranged to leave a space that does not allow a distal end of the first finger placed on the upper surface finger-resting portion to come in contact with the locking hook portion when the insertion portion is fitted into the receiving-side connector.

* * * * *